US011369551B2

(12) United States Patent
Dolan et al.

(10) Patent No.: US 11,369,551 B2
(45) Date of Patent: Jun. 28, 2022

(54) ORAL CARE COMPOSITIONS WITH IMPROVED TIN COMPATABILITY

(71) Applicant: The Procter & Gamble Company, Cincinnati, OH (US)

(72) Inventors: Lawrence Edward Dolan, Cincinnati, OH (US); William Michael Glandorf, Mason, OH (US); Sanjeev Midha, Mason, OH (US); Eva Schneiderman, Mason, OH (US); Carl E. Catrenich, Fairfield, OH (US); Marianne Zsiska, Middletown, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 89 days.

(21) Appl. No.: 16/701,672

(22) Filed: Dec. 3, 2019

(65) Prior Publication Data
US 2020/0170897 A1   Jun. 4, 2020

Related U.S. Application Data

(60) Provisional application No. 62/774,899, filed on Dec. 4, 2018.

(51) Int. Cl.
| | |
|---|---|
| *A61Q 11/00* | (2006.01) |
| *A61K 8/25* | (2006.01) |
| *A61K 8/02* | (2006.01) |
| *A61K 8/21* | (2006.01) |
| *A61K 9/14* | (2006.01) |
| *A61K 6/00* | (2020.01) |
| *A61K 8/24* | (2006.01) |
| *A61K 8/37* | (2006.01) |
| *A61K 8/55* | (2006.01) |
| *G01N 21/80* | (2006.01) |

(52) U.S. Cl.
CPC ............... *A61K 8/21* (2013.01); *A61K 8/025* (2013.01); *A61K 8/0279* (2013.01); *A61K 8/24* (2013.01); *A61K 8/25* (2013.01); *A61K 8/37* (2013.01); *A61K 8/55* (2013.01); *A61Q 11/00* (2013.01); *G01N 21/80* (2013.01); *A61K 2800/28* (2013.01); *A61K 2800/412* (2013.01)

(58) Field of Classification Search
CPC ... A61K 8/21; A61K 8/24; A61K 8/27; A61K 8/25; A61K 2800/92; A61K 2800/48; A61K 2800/412; A61K 2800/30; A61K 8/0241; A61K 2300/00; A61K 2800/28; A61K 2800/60; A61Q 11/00; A61Q 17/005
See application file for complete search history.

(56) References Cited

U.S. PATENT DOCUMENTS

| | | | |
|---|---|---|---|
| 4,340,583 A | 7/1982 | Wason | |
| 4,420,312 A | 12/1983 | Wason | |
| 5,833,952 A * | 11/1998 | Grigor | A61K 8/24 424/49 |
| 6,946,119 B2 * | 9/2005 | Gallis | A61K 8/25 423/335 |
| 7,255,852 B2 | 8/2007 | Gallis | |
| 7,438,895 B2 | 10/2008 | Gallis | |
| 8,211,406 B2 | 7/2012 | Baig | |
| 8,211,407 B2 | 7/2012 | Deckner | |
| 8,211,408 B2 | 7/2012 | Baig | |
| 8,211,409 B2 | 7/2012 | Baig | |
| 8,211,410 B2 | 7/2012 | Baig | |
| 8,211,411 B2 | 7/2012 | Deckner | |
| 8,216,552 B2 | 7/2012 | Deckner | |
| 8,216,553 B2 | 7/2012 | Hughes | |
| 8,221,722 B2 | 7/2012 | Baig | |
| 8,221,723 B2 | 7/2012 | Deckner | |
| 8,221,724 B2 | 7/2012 | Hughes | |
| 8,221,725 B2 | 7/2012 | Deckner | |
| 8,221,726 B2 | 7/2012 | Deckner | |
| 8,226,932 B2 | 7/2012 | Haught | |
| 8,293,216 B2 | 10/2012 | Deckner | |
| 8,551,457 B2 | 10/2013 | Deckner | |
| 8,795,637 B2 | 8/2014 | Deckner | |
| 2004/0086466 A1 * | 5/2004 | Glandorf | A61Q 11/00 424/49 |
| 2004/0161389 A1 | 8/2004 | Gallis et al. | |
| 2004/0161390 A1 | 8/2004 | Gallis et al. | |
| 2005/0032965 A1 | 2/2005 | Valero | |
| 2006/0140881 A1 | 6/2006 | Xu | |
| 2008/0160052 A1 * | 7/2008 | Gallis | A61K 8/25 424/401 |
| 2010/0135921 A1 | 6/2010 | Hughes | |

(Continued)

FOREIGN PATENT DOCUMENTS

| | | |
|---|---|---|
| AU | 2007201912 A1 | 5/2007 |
| EP | 2057978 A1 | 5/2009 |
| EP | 2246031 A1 | 11/2010 |
| WO | 03045344 A2 | 6/2003 |
| WO | 2007062365 A2 | 5/2007 |
| WO | WO2015171836 A1 | 11/2015 |
| WO | WO2018114280 A1 | 6/2018 |

OTHER PUBLICATIONS

14632_PCT_Search_Report and Written Opinion for PCT/US2017064202 dated Dec. 1, 2017.

(Continued)

*Primary Examiner* — Tracy Liu
(74) *Attorney, Agent, or Firm* — Parker D. McCrary

(57) ABSTRACT

Oral care compositions with silica particles and stannous fluoride with an improved tin compatibility are disclosed. Oral care compositions with silica particles and stannous fluoride with a low level of an additional tin compound are disclosed. Oral care compositions with substantially spherical silica particles are disclosed.

14 Claims, 2 Drawing Sheets

(56) References Cited

U.S. PATENT DOCUMENTS

| | | | |
|---|---|---|---|
| 2011/0206746 A1* | 8/2011 | Hagar | C01B 33/193 |
| | | | 424/401 |
| 2011/0239736 A1 | 10/2011 | Ramji | |
| 2014/0127145 A1* | 5/2014 | Deckner | C01B 33/18 |
| | | | 424/57 |
| 2018/0168958 A1 | 6/2018 | Dolan | |
| 2018/0168962 A1 | 6/2018 | Rege | |
| 2019/0183748 A1 | 6/2019 | Bhadra | |

OTHER PUBLICATIONS

15423 PCT Search Report and Written Opinion for PCT/US2019/064100 dated Sep. 1, 2020.

* cited by examiner

ORAL CARE COMPOSITIONS WITH IMPROVED TIN COMPATABILITY

FIELD OF THE INVENTION

The present invention relates to compositions with improved tin compatibility, reduced levels of additional tin compounds, and/or low surface area silica particles. The present invention also relates to methods for determining the antimicrobial efficacy of a composition.

BACKGROUND OF THE INVENTION

Compositions with tin, including stannous fluoride, are used in toothpaste and other dentifrice applications. Stannous-based dentifrice compositions provide therapeutic benefits, such as improved cavity protection and reduced plaque, gingivitis, and tooth sensitivity. However, the effectiveness of stannous in dentifrice compositions can be diminished due to interactions with other components of the formulation, such as silica particles.

Low water or anhydrous dentifrice formulations have been used to increase tin compatibility, but these chassis can have a high formulation cost. Alternative abrasives, such as synthetic polymeric abrasives, heat treated precipitated silica, fused silica, and surface treated silicas, have been utilized to improve compatibility with soluble tin ions, but these abrasives have safety challenges, high abrasion, and/or lack surface durability.

Additional tin compounds can be added to dentifrice compositions to increase the amount of available tin ions. However, the addition of additional tin compounds can increase the complexity and cost of the dentifrice chassis. Therefore, it would be beneficial to provide silica materials with improved tin compatibility to improve the overall effectiveness of the tin in a dentifrice composition without the need to add additional tin compounds.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Oral care compositions having silica particles with increased tin compatibility and decreased amounts of additional tin compounds.

An oral care composition is provided with at least (a) stannous fluoride, (b) less than about 0.2%, by weight of the composition, of an additional tin compound; and (c) from about 10% to about 50%, by weight of the composition of an abrasive, wherein the abrasive comprises silica particles.

An oral care composition is provided with at least (a) stannous fluoride; (b) less than about 0.2%, by weight of the composition, of an additional tin compound; and (c) from about 10% to about 50%, by weight of the composition of an abrasive, wherein the abrasive comprises silica particles with a BET surface area of from 0 to about 10 $m^2/g$.

A method for reducing plaque, gingivitis, or tooth sensitivity of a subject comprising (a) providing a dentifrice composition with stannous fluoride, less than about 0.2%, by weight of the composition, of an additional tin compound; and from about 10% to about 50%, by weight of the composition of an abrasive, wherein the abrasive comprises silica particles with a BET surface area of from 0 to about 10 $m^2/g$; and (b) contacting the subject's oral cavity with the dentifrice composition.

A method for determining the antimicrobial efficacy of a composition, the method comprising (a) providing a first container comprising: (i) a main chamber comprising a liquid growth media, and (ii) a second chamber comprising agar and a pH indicator dye; (b) adding a source of microorganisms to the main chamber of the first container; (c) measuring a first detection time of a colorimetric reaction of the pH indicator dye in the second chamber of the first container; (d) providing a second container comprising: (i) a main chamber comprising a liquid growth media, and (ii) a second chamber comprising agar and a pH indicator dye; (e) adding the source of microorganisms and the composition comprising an antimicrobial agent to the main chamber of the second chamber; (f) measuring a second detection time of a colorimetric reaction of the pH indicator dye in the second chamber of the second container; (g) comparing the first detection time and the second detection to determine the antimicrobial efficacy of the composition.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

DETAILED DESCRIPTION OF THE INVENTION

Figure 1:
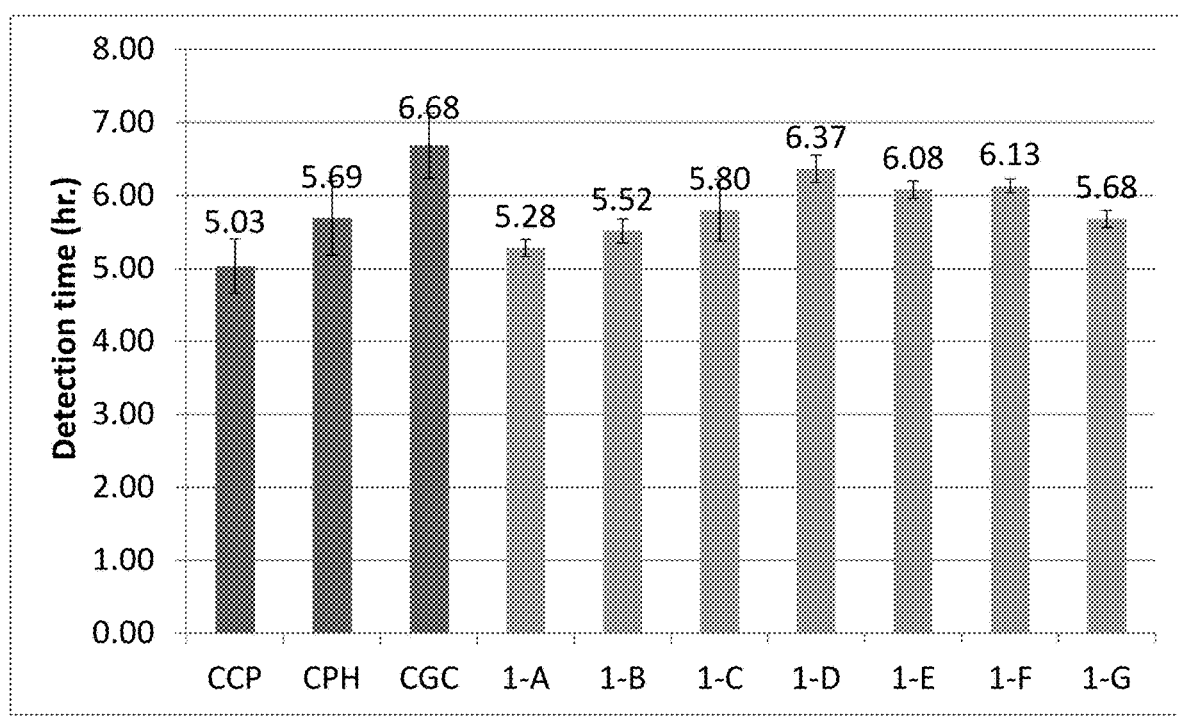
FIG. 1 is a graph showing the salivary bacteria inhibition of 1-A through 1-G.

The present invention is directed to oral care compositions having precipitated silica particles that can be characterized by a BET surface area in a range from 0 to about 10 $m^2/g$ (or from about 0.05 to about 8 $m^2/g$), a total mercury intrusion pore volume in a range from about 0.2 to about 1.5 cc/g, and/or a d50 median particle size in a range from about 4 to about 25 µm. Oral care compositions having silica particles that have a lower surface area can show an increased compatibility with tin. Thus, oral care compositions having silica particles with a lower surface area can have decreased levels of additional tin compounds, which can lead to dentifrice chassis with decreased complexity and cost. Without wishing to be bound by theory, it is believed that a lower surface area limits the number of interactions between soluble tin ions and the surface of silica particles, which can limit tin bioavailability. Methods of making oral care compositions with decreased levels of additional tin compounds are also disclosed herein.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied.

The term "oral care composition", as used herein, includes a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice, tooth gel, subgingival gel, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

The term "dentifrice", as used herein, includes tooth or subgingival-paste, gel, or liquid formulations unless otherwise specified. The dentifrice composition may be a single-phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

"Active and other ingredients" useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

While compositions and methods are described herein in terms of "comprising" various components or steps, the compositions and methods can also "consist essentially of" or "consist of" the various components or steps, unless stated otherwise.

As used herein, the word "or" when used as a connector of two or more elements is meant to include the elements individually and in combination; for example, X or Y, means X or Y or both.

As used herein, the articles "a" and "an" are understood to mean one or more of the material that is claimed or described, for example, "an oral care composition" or "a bleaching agent."

All measurements referred to herein are made at about 23° C. (i.e. room temperature) unless otherwise specified.

Generally, groups of elements are indicated using the numbering scheme indicated in the periodic table of elements. In some instances, a group of elements can be indicated using a common name assigned to the group; for example, alkali metals for Group 1 elements, alkaline earth metals for Group 2 elements, and so forth.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. As a representative example, the BET surface area of the silica particles can be in certain ranges in various aspects of this invention. By a disclosure that the BET surface area is in a range from 0 to about 10 $m^2/g$, the intent is to recite that the surface area can be any surface area within the range and, for example, can be equal to about 0.1, about 0.5, about 1, about 2, about 3, about 4, about 5, about 6, about 7, about 8, about 9, or about 10 $m^2/g$. Additionally, the surface area can be within any range from 0 to about 10 $m^2/g$ (for example, from about 0.05 to about 8 $m^2/g$), and this also includes any combination of ranges between 0 and about 10 $m^2/g$ (for example, the surface area can be in a range from about 0.1 to about 3, or from about 5 to about 7 $m^2/g$). Likewise, all other ranges disclosed herein should be interpreted in a manner similar to this example.

The term "about" means that amounts, sizes, formulations, parameters, and other quantities and characteristics are not and need not be exact, but can be approximate and/or larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

The terms "soluble tin ions" and "tin ions," refer to a tin (Sn) atoms or molecules with a net electric charge due to the loss or gain of one or more electrons. Soluble tin ions include stannous ($Sn^{2+}$), stannic ($Sn^{4+}$), and any other ion generated from a compound comprising tin when dissolved in one or more solvents.

The oral care composition can be in any suitable form, such as a solid, liquid, powder, paste, or combinations thereof. The components of the oral care composition can be incorporated into a film, a strip, a foam, or a fiber-based oral care composition. The oral care composition can include a variety of active and inactive ingredients, such as, for example, but not limited to low surface area silica particles, stannous fluoride, low levels of an additional tin compound, water, a humectant, additional abrasives, thickening agents, tooth whitening actives, teeth color modifying substances, a therapeutic agent, a surfactant, a polyphosphate source, other ingredients, and the like, as well as any combination thereof, as described below.

Low Surface Area Silica Particles

The oral care composition of the present invention comprises an abrasive comprising silica particles. An illustrative and non-limiting example of silica particles consistent with the present invention can have the following characteristics: (i) a d50 median particle size of from about 4 to about 25 μm, (ii) a sphericity factor ($S_{80}$) of greater than or equal to about 0.9, (iii) a BET surface area of from 0 to about 10 $m^2/g$, and/or (iv) a total mercury intrusion pore volume of from about 0.2 to about 1.5 cc/g. Another illustrative and non-limiting example of silica particles consistent with the present invention can have the following characteristics: (i) a d50 median particle size of from about 6 to about 25 μm, (ii) a sphericity factor ($S_{80}$) of greater than or equal to about 0.9, (iii) a BET surface area of from 0 to about 8 $m^2/g$, and/or (iv) a total mercury intrusion pore volume of from about 0.35 to about 1.1 cc/g. Yet another illustrative and non-limiting example of silica particles consistent with the present invention can have the following characteristics: (i) a d50 median particle size of from about 8 to about 20 μm, (ii) a sphericity factor ($S_{80}$) of greater than or equal to about 0.9, (iii) a BET surface area of from 0 to about 8 m$^2$/g, and/or (iv) a total mercury intrusion pore volume of from about 0.35 to about 0.7 cc/g. In further aspects, such silica particles consistent with the present invention also can have any of the characteristics or properties provided below, and in any combination.

The low surface area silica particles can have a relatively large average particle size. Often, the median particle size (d50) and/or mean particle size (average) can be from about 4 to about 25, from about 4 to about 20, from about 6 to about 25, from about 6 to about 22, from about 6 to about 18, from about 7 to about 25, from about 7 to about 20, or from about 7 to about 18 μm, and the like. The median particle size (d50) and/or mean particle size (average) can be from about 8 to about 25, from about 8 to about 20, from about 8 to about 18, from about 8 to about 15, from about 9 to about 16, or from about 9 to about 14 μm. Other appropriate ranges for the mean and median particle sizes are readily apparent from this disclosure.

The low surface area particles can also have a very narrow particle size distribution, which can be quantified by the ratio of (d90−d10)/d50. A lower value for the ratio indicates a narrower particle size distribution, while a larger value for the ratio indicates a broader particle size distribution. Generally, the low surface area particles disclosed herein can be characterized by a ratio of (d90−d10)/d50 in a range from about 1.1 to about 2.4. The ratio of (d90−d10)/d50 can be from about 1.1 to about 2.2, while in another aspect, the ratio of (d90−d10)/d50 can be from about 1.1 to about 2, from about 1.1 to about 1.7, or from about 1.3 to about 1.5. The ratio of (d90−d10)/d50 can be from about 1.2 to about 2.4, while in still another aspect, the ratio of (d90−d10)/d50 can be from about 1.2 to about 2.2, or from about 1.2 to about 2. Other appropriate ranges for the ratio of (d90−d10)/d50 are readily apparent from this disclosure.

Another indicator of the narrow particle size distribution of the low surface area silica particles is the weight percentage of 325 mesh residue (amount retained in a 325 mesh sieve), which can be less than or equal to about 1.2 wt. %. The 325 mesh residue can be less than or equal to about 1 wt. %, less than or equal to about 0.75 wt. %, less than or equal to about 0.6 wt. %, or less than or equal to about 0.3 wt. %. Other appropriate ranges for the 325 mesh residue are readily apparent from this disclosure.

Sphericity of the low surface area silica particles can be quantified by a sphericity factor ($S_{80}$), which can be greater than or equal to about 0.85, greater than or equal to about 0.88, or greater than or equal to about 0.9. The sphericity factor ($S_{80}$) is determined as follows. An SEM image of the silica particle sample is magnified 20,000 times, which is representative of the silica particle sample, and is imported into photo imaging software, and the outline of each particle (two-dimensionally) is traced. Particles that are close in proximity to one another but not attached to one another should be considered separate particles for this analysis. The outlined particles are then filled in with color, and the image is imported into particle characterization software (e.g., IMAGE-PRO PLUS available from Media Cybernetics, Inc., Bethesda, Md.) capable of determining the perimeter and area of the particles. Sphericity of the particles can then be calculated according to the equation, Sphericity=(perimeter)$^2$ divided by (4π×area), wherein perimeter is the software measured perimeter derived from the outlined trace of the particles, and wherein area is the software measured area within the traced perimeter of the particles.

The sphericity calculation is performed for each particle that fits entirely within the SEM image. These values are then sorted by value, and the lowest 20% of these values are discarded. The remaining 80% of these values are averaged to obtain the sphericity factor ($S_{80}$). Additional information on sphericity can be found in U.S. Pat. Nos. 8,945,517 and 8,609,068, incorporated herein by reference in their entirety.

The low surface area silica particles can have a sphericity factor ($S_{80}$) greater than or equal to about 0.85, or greater than or equal to about 0.88, while in another aspect, the sphericity factor ($S_{80}$) can be greater than or equal to about 0.9. The low surface area silica particles can be characterized by a sphericity factor ($S_{80}$) greater than or equal to about 0.92, and in still another aspect, the silica particles can be characterized by a sphericity factor ($S_{80}$) greater than or equal to about 0.94. As one of skill in the art would readily recognize, a 3-dimensional sphere (or 2-dimensional circle) will have a sphericity factor ($S_{80}$) equal to 1.

In an aspect, the low surface area silica particles can have a very low surface area, generally a BET surface area of from 0 to about 10 m$^2$/g. The BET surface area can be from about 0.05 to about 10, from about 0.1 to about 10, from about 0.25 to about 10, or from about 0.05 to about 8 m$^2$/g. The BET surface area can be from about 0.25 to about 8, from about 0.5 to about 8, from about 0.1 to about 5, from about 0.25 to about 5, from about 0.5 to about 5, from about 0.25 to about 3.5, or from about 0.5 to about 2 m$^2$/g, and the like. The BET surface area also can be from 0 to about 8 m$^2$/g, from 0 to about 5 m$^2$/g, or from 0 to about 3 m$^2$/g. Other appropriate ranges for the BET surface area are readily apparent from this disclosure.

The total mercury intrusion pore volume of the low surface area silica particles can be relatively low, such as from about 0.2 to about 1.5, from about 0.3 to about 1.1, from about 0.35 to about 1.1, from about 0.35 to about 0.7, from about 0.35 to about 0.65, from about 0.35 to about 0.62, or from about 0.35 to about 0.6 cc/g. The total mercury intrusion pore volume of the low surface area silica particles can be from about 0.4 to about 0.7 cc/g, from about 0.4 to about 0.65 cc/g, from about 0.45 to about 0.65 cc/g, or from about 0.49 to about 0.6 cc/g. Other appropriate ranges for the total mercury intrusion pore volume are readily apparent from this disclosure.

Additionally, the low surface area silica particles can be less abrasive, as reflected by an Einlehner abrasion value from about 7 to about 25 mg lost/100,000 revolutions. For instance, the Einlehner abrasion value can from about 8 to about 20; alternatively, from about 10 to about 20; or alternatively, from about 15 to about 22 mg lost/100,000 revolutions. The Einlehner abrasion value also can be in a range from about 10 to about 25 mg lost/100,000 revolutions, from about 10 to about 22 mg lost/100,000 revolutions, or from about 11 to about 17 mg lost/100,000 revolutions. Other appropriate ranges for the Einlehner abrasion value are readily apparent from this disclosure.

The low surface area silica particles can also have a relatively high pour density. The pour density can be from about 30 to about 65 lb/ft$^3$, or from about 40 to about 65 lb/ft$^3$. The pour density can be from about 40 to about 62 lb/ft$^3$, from about 42 to about 60 lb/ft$^3$, or from about 43 to about 58 lb/ft$^3$. The pour density can be from about 42 to about 56 lb/ft$^3$, or from about 44 to about 54 lb/ft$^3$. Other appropriate ranges for the pour density are readily apparent from this disclosure.

The low surface area silica particles in accordance with aspects of this invention can have excellent tin and/or stannous compatibility and excellent CPC compatibility.

Typically, the low surface area silica particles described herein have a tin and/or stannous compatibility from about 40 to about 99%, such as, for instance, from about 80 to about 99%, from about 75 to about 98%, from about 75 to about 95%, from about 80 to about 95%, from about 82 to about 98%, or from about 86 to about 93%, and the like. Additionally, the low surface area silica particles typically have a CPC compatibility from about 55 to about 99%, such as, for instance, from about 40 to about 95%, from about 75 to about 95%, from about 78 to about 95%, or from about 81 to about 91%, and the like. Other appropriate ranges for the tin and/or stannous compatibility and CPC compatibility are readily apparent from this disclosure.

In another aspect, the low surface area silica particles can have relatively low oil absorption, relatively low water absorption, and very low CTAB surface area. For instance, the oil absorption can be in a range from about 20 to about 75 cc/100 g, from about 25 to about 60 cc/100 g, from about 25 to about 55 cc/100 g, or from about 32 to about 50 cc/100 g. Additionally or alternatively, the water absorption can be in a range from about 40 to about 75 cc/100 g, from about 45 to about 72 cc/100 g, from about 50 to about 70 cc/100 g, from about 50 to about 65 cc/100 g, or from about 57 to about 66 cc/100 g. Representative and non-limiting ranges for the CTAB surface include from 0 to about 10 $m^2/g$, from 0 to about 6 $m^2/g$, from 0 to about 4 $m^2/g$, or from 0 to about 2 $m^2/g$. Other appropriate ranges for the oil absorption, the water absorption, and the CTAB surface area are readily apparent from this disclosure.

While not limited thereto, the disclosed low surface area silica particles can have a loss on drying (LOD) of from about 1 to about 10 wt. %. Illustrative and non-limiting ranges for the LOD include from about 1 to about 8 wt. %, from about 2 to about 8 wt. %, from about 1 to about 7 wt. %, from about 1 to about 5 wt. %, from about 1 to about 4 wt. %, or from about 1.5 to about 2 wt. %. Likewise, while not limited thereto, the disclosed spherical silica particles can have a loss on ignition (LOI) that often falls within a range from about 3 to about 10 wt. %. Illustrative and non-limiting ranges for the LOI include from about 3 to about 8 wt. %, from about 3 to about 7 wt. %, from about 3 to about 6 wt. %, from about 3.5 to about 9 wt. %, from about 3.5 to about 7.5 wt. %, or from about 3.5 to about 6 wt. %. Other appropriate ranges for the LOD and LOI are readily apparent from this disclosure.

Generally, the low surface area silica particles can have a substantially neutral pH that can be from about 5.5 to about 9, from about 6.2 to about 8.5, or from about 6.8 to about 8.2. Other appropriate ranges for the pH are readily apparent from this disclosure.

The Relative Dentin Abrasion (RDA) test is typically performed to confirm that a dentifrice composition, e.g., toothpaste, is safe for consumer use, with the upper limit of the test set at 250. Unexpectedly, the results provided herein demonstrate that, for the low surface area silica particles consistent with this invention, the RDA generally decreases as the median particle size (d50) and/or mean particle size (average) increases. Oral care compositions comprising the low surface area silica particles can be characterized by a RDA at 20 wt. % loading of less than about 250, from about 100 to about 220, or from about 120 to about 200. Other illustrative and non-limiting ranges for the RDA at 20 wt. % loading can include from about 50 to about 200, from about 80 to about 200, from about 80 to about 150, from about 130 to about 190, from about 130 to about 180, from about 150 to about 200, from about 150 to about 190, or from about 168 to about 182. Other appropriate ranges for the RDA are readily apparent from this disclosure.

The low surface area silica particles also can be described by their Pellicle Cleaning Ratio (PCR), which is a measure of the cleaning characteristics of a dentifrice composition containing the silica particles. The low surface area silica particles can be characterized by a PCR at 20 wt. % loading of about 70 to about 130, from about 80 to about 130, from about 70 to about 120, from about 80 to about 120, or from about 90 to about 110. The PCR/RDA ratio (at 20 wt. % loading) can be from about 0.4:1 to about 1.1:1, from about 0.4:1 to about 0.8:1, from about 0.5:1 to about 1:1, from about 0.5:1 to about 0.7:1, from about 0.45:1 to about 0.65:1, or from about 0.56:1 to about 0.57:1.

The low surface area silica particles can be amorphous, can be synthetic, or can be both amorphous and synthetic. Moreover, the low surface area silica particles can comprise (or consist essentially of, or consist of) precipitated silica particles in particular aspects of this invention, although not limited thereto.

The low surface area silica particles can be spherical, substantial spherical, cubic, cylindrical, rectangular, triangular, or any three-dimensional shape that minimizes the surface area of the low surface area silica particles.

The low surface area silica particles can be used in any suitable composition and for any suitable end-use application. Often, the low surface area silica particles can be used in oral care applications, such as in a dentifrice composition. The dentifrice composition can contain any suitable amount of the low surface area silica particles, such as from about 0.5% to about 50%, from about 1% to about 50%, from about 5% to about 35%, from about 10% to about 40%, or from about 10% to about 30%, by weight of the oral care composition, of the low surface area silica particles.

Stannous Fluoride

The oral care composition of the present invention comprises stannous fluoride. The oral care composition can comprise stannous fluoride in an amount capable of providing from about 50 ppm to about 3500 ppm, and preferably from about 500 ppm to about 3000 ppm of free fluoride ions. To deliver the desired amount of fluoride ions, stannous fluoride may be present in the total dentifrice composition at an amount of from about 0.0025% to about 5%, from about 0.2% to about 1%, from about 0.5% to about 1.5%, or from about 0.3% to about 0.6%, by weight of the total oral care composition. Other sources of fluoride ions may be present, such as, for example, sodium fluoride, potassium fluoride, amine fluoride, sodium monofluorophosphate, and/or zinc fluoride.

Additional Tin Compounds

The oral care composition of the present invention has a low level or is free of an additional tin compound. In many dentifrice compositions comprising stannous fluoride and a silica abrasive, additional tin compounds are added to increase the amount and/or availability of soluble tin ions. Additional tin compounds, as used herein, describe tin compounds that do not have a source of free fluoride ions (i.e. $SnF_2$, $SnF_4$, among others would not be additional tin compounds). Without wishing to be bound by theory, it is believed that the soluble tin ions provided by stannous fluoride interact with the surface of silica particles, which lowers the amount of soluble tin ions available to provide a therapeutic benefit to the oral cavity. In many dentifrice compositions, an additional tin compound is added to increase the amount of soluble tin ions present.

Without wishing to be bound by theory, it is believed that by using the low surface area silica particles, the tin bioavailability is increased such that a lower level of the additional tin compound may be used. The oral care composition can comprise less than about 0.5%, less than about 0.2%, less than about 0.1%, less than about 0.05%, or less than about 0.01%, by weight of the total oral care composition, of the additional tin compound.

The additional tin compound can comprise stannous chloride, stannous bromide, stannous iodide, stannous hydroxide, stannous oxide, stannic bromide, stannic chloride, stannic iodide, stannic sulfide, or any other tin compound not capable of providing a free fluoride ion in solution.

Fluoride Ion Source and Stannous Chloride

The oral care composition of the present invention can also comprise a non-stannous fluoride ion source in combination with stannous chloride. In this embodiment, a lower level of stannous chloride can be added when combined with the low surface area silica particles, as described herein. A suitable non-stannous fluoride ion source can comprise one or more fluoride containing compounds, such as sodium fluoride, potassium fluoride, amine fluoride, sodium monofluorophosphate, zinc fluoride, and/or mixtures thereof. The oral care composition can comprise the fluoride ion source capable of providing from about 50 ppm to about 5000 ppm, and preferably from about 500 ppm to about 3000 ppm of free fluoride ions. To deliver the desired amount of fluoride ions, the fluoride ion source may be present in the oral care composition at an amount of from about 0.0025% to about 5%, from about 0.01% to about 5%, from about 0.01% to about 10%, from about 0.2% to about 1%, from about 0.5% to about 1.5%, or from about 0.3% to about 0.6%, by weight of the oral care composition.

In this embodiment, the oral care composition can comprise stannous chloride in combination with the non-stannous fluoride ion source Without wishing to be bound by theory, it is believed that the soluble tin ions provided by stannous chloride interact with the surface of silica particles, which lowers the amount of soluble tin ions available to provide a therapeutic benefit to the oral cavity. In many dentifrice compositions, higher levels of stannous chloride can be added to increase the amount of soluble tin ions present.

Without wishing to be bound by theory, it is believed that by using the low surface area silica particles, the tin bioavailability is increased such that a lower level of the stannous chloride may be used. The oral care composition can comprise from about 0.01% to about 1%, from about 0.01% to about 0.5%, from about 0.01% to about 0.2%, less than about 0.5%, less than about 0.2%, less than about 0.1%, less than about 0.05%, or less than about 0.01%, by weight of the total oral care composition, of the stannous chloride.

Water

The oral care composition of the present invention can be anhydrous, a low water formulation, or a high-water formulation. In total, the oral care composition can comprise from 0% to about 75%, by weight of the composition, of water. Preferably, the water is USP water.

In a high-water formulation, the oral care composition comprises from about 45% to about 75%, by weight of the composition, of water. The high water oral care composition can comprise from about 45% to about 65%, from about 45% to about 55%, or from about 46% to about 54%, by weight of the composition, of water. The water may be added to the high-water formulation and/or may come into the composition from the inclusion of other ingredients.

In a low water formulation, the oral care composition comprises from about 10% to about 45%, by weight of the composition, of water. The low water oral care composition can comprise from about 10% to about 35%, from about 15% to about 25%, or from about 20% to about 25%, by weight of the composition, of water. The water may be added to the low water formulation and/or may come into the composition from the inclusion of other ingredients.

In an anhydrous formulation, the oral care composition comprises less than about 10%, by weight of the composition, of water. The anhydrous oral care composition comprises less than 5%, less than 1%, or 0%, by weight of the composition, of water. The water may be added to the anhydrous formulation and/or may come into the composition from the inclusion of other ingredients.

Humectants

The oral care composition can comprise a humectant, have low levels of a humectant, or be free of a humectant. Humectants serve to add body or "mouth texture" to an oral care composition or dentifrice as well as preventing the dentifrice from drying out. Suitable humectants include polyethylene glycol (at a variety of different molecular weights), propylene glycol, glycerin (glycerol), erythritol, xylitol, sorbitol, mannitol, lactitol, and hydrogenated starch hydrolyzates, and mixtures thereof. The oral care composition can comprise amount from 0 to about 70%, from about 10% to about 60%, or from about 25% to about 60%, by weight of the oral care composition, of a humectant.

Abrasive

The oral care composition can comprise the disclosed low surface area silica particles alone as the abrasive or as an additive or co-abrasive with other abrasive materials discussed herein or known in the art. Thus, any number of other conventional types of abrasive additives can be present within the dentifrice compositions of the invention. Other such abrasive particles include, for example, precipitated calcium carbonate (PCC), ground calcium carbonate (GCC), chalk, bentonite, dicalcium phosphate or its dihydrate forms, silica gel (by itself, and of any structure), precipitated silica, amorphous precipitated silica (by itself, and of any structure as well), perlite, titanium dioxide, dicalcium phosphate, calcium pyrophosphate, alumina, hydrated alumina, calcined alumina, aluminum silicate, insoluble sodium metaphosphate, insoluble potassium metaphosphate, insoluble magnesium carbonate, zirconium silicate, particulate thermosetting resins and other suitable abrasive materials. Such materials can be introduced into the oral care compositions to tailor the polishing characteristics of the target formulation.

Thickening Agents

The oral care composition can comprise thickening agents. Thickening agents can be useful in the dentifrice compositions to provide a gelatinous structure that stabilizes the toothpaste against phase separation. Suitable thickening agents include polysaccharides and silica thickeners. Some non-limiting examples of polysaccharides include starch; glycerite of starch; gums such as gum karaya (sterculia gum), gum tragacanth, gum arabic, gum ghatti, gum acacia, xanthan gum, guar gum and cellulose gum; magnesium aluminum silicate (Veegum); carrageenan; sodium alginate; agar-agar; pectin; gelatin; cellulose compounds such as cellulose, carboxymethyl cellulose, hydroxyethyl cellulose, hydroxypropyl cellulose, hydroxymethyl cellulose, hydroxymethyl carboxypropyl cellulose, methyl cellulose, ethyl cellulose, and sulfated cellulose; natural and synthetic clays such as hectorite clays; and mixtures thereof.

The thickening agent can comprise polysaccharides. Polysaccharides that are suitable for use herein include carageenans, gellan gum, locust bean gum, xanthan gum, carbomers, poloxamers, modified cellulose, and mixtures thereof. Carageenan is a polysaccharide derived from seaweed. There are several types of carageenan that may be distinguished by their seaweed source and/or by their degree of and position of sulfation. The thickening agent can comprise kappa carageenans, modified kappa carageenans, iota carageenans, modified iota carageenans, lambda carrageenan, and mixtures thereof. Carageenans suitable for use herein include those commercially available from the FMC Company under the series designation "Viscarin," including but not limited to Viscarin TP 329, Viscarin TP 388, and Viscarin TP 389.

The thickening agent can comprise inorganic thickening agents. Some non-limiting examples of suitable inorganic thickening agents include colloidal magnesium aluminum silicate, silica thickeners. Useful silica thickeners include, for example, include, as a non-limiting example, an amorphous precipitated silica such as ZEODENT® 165 silica. Other non-limiting silica thickeners include ZEODENT® 153, 163, and 167, and ZEOFREE® 177 and 265 silica products, all available from Evonik Corporation, and AEROSIL® fumed silicas.

Silica thickeners can interact with soluble tin ions provided by dentifrice compositions comprising stannous fluoride. Without wishing to be bound by theory, it is believed that the use of low surface area silica allows for the incorporation of increased amounts of thickening silica because of the higher amounts of soluble tin ions present in dentifrice compounds comprising low surface area silica.

The oral care composition can comprise from 0% to about 15%, from 0.1% to about 10%, from about 0.2% to about 5%, or from about 0.5% to about 2% of one or more thickening agents.

Tooth Whitening Actives and Teeth Color Modifying Substances

The oral care composition can comprise bleaching or oxidizing agents, such as peroxides, perborates, percarbonates, peroxyacids, persulfates, metal chlorites, and mixtures thereof. Suitable peroxide compounds include hydrogen peroxide, urea peroxide, calcium peroxide, and mixtures thereof. A preferred percarbonate is sodium percarbonate. Other suitable whitening agents include potassium, ammonium, Sodium and lithium persulfates and perborate mono- and tetrahydrates, and sodium pyrophosphate peroxyhydrate. Suitable metal chlorites include calcium chlorite, barium chlorite, magnesium chlorite, lithium chlorite, sodium chlorite, and potassium chlorite. The preferred chlorite is sodium chlorite. Additional whitening actives may be hypochlorite and chlorine dioxide.

The oral care composition can comprise teeth color modifying substances. The teeth color modifying substances are suitable for modifying the color of the teeth to satisfy the consumer. The teeth color modifying substances comprise particles that when applied on the tooth surface modify that surface in terms of absorption and, or reflection of light. Such teeth color modifying particles provide an appearance benefit when a film containing such particles is applied over the Surfaces of a tooth or teeth. Particles most useful in the present invention include pigments and colorants routinely used in the cosmetic arts. Pigments and colorants include inorganic white pigments, inorganic colored pigments, pearling agents, filler powders and the like. Specific examples can be talc, mica, magnesium carbonate, calcium carbonate, magnesium silicate, aluminum magnesium silicate, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. Most preferred are those selected from the group consisting of titanium dioxide, bismuth oxychloride, zinc oxide and mixtures thereof. Pigments that are generally recognized as Safe, and are listed in C.T.F.A. Cosmetic Ingredient Handbook, 3rd Ed., Cosmetic and Fragrance Assn., Inc., Washington D.C. (1982). The pigments are typically used as opacifiers and colorants. These pigments can be used as treated particles, or as the raw pigments themselves. Typical pigment levels are selected for the particular impact that is desired by the consumer. For example, for teeth that are particularly dark or stained one would typically use pigments in sufficient amount to lighten the teeth. On the other hand, where individual teeth or Spots on the teeth are lighter than other teeth, pigments to darken the teeth may be useful.

The oral care composition can comprise from about 0.05% to about 20%, from about 0.10% to about 15%, or from about 0.25% to about 10%, by weight of the composition, of one or more tooth whitening and/or tooth color modifying substances.

Therapeutic Agents

The oral care composition can comprise other therapeutic agents in addition to stannous fluoride. Therapeutic agents can be used to provide for the prevention and treatment of periodontal disease and/or temperature sensitivity, for example. Suitable therapeutic agents can include, but are not limited to, condensed phosphates, such as tetrasodium pyrophosphate, tetrapotassium pyrophosphate, disodium dihydrogen pyrophosphate, trisodium monohydrogen pyrophosphate; tripolyphosphates, hexametaphosphates, trimetaphosphates and pyrophosphates; antimicrobial agents such as triclosan, zinc based salts, such zinc lactate and/or zinc citrate, bisguanides, such as alexidine, chlorhexidine and chlorhexidine gluconate; enzymes such as papain, bromelain, glucoamylase, amylase, dextranase, mutanase, lipases, pectinase, tannase, and proteases; quaternary ammonium compounds, such as benzalkonium chloride (BZK), benzethonium chloride (BZT), cetylpyridinium chloride (CPC), and domiphen bromide; sanguinaria extract and sanguinarine; volatile oils, such as eucalyptol, menthol, thymol, and methyl salicylate; amine fluorides; peroxides and the like. Therapeutic agents can be used in dentifrice formulations singly or in combination, and at any therapeutically safe and effective level or dosage.

Surfactants

The oral care composition can comprise one or more surfactants. The surfactants can be used to make the compositions more cosmetically acceptable. The surfactant is preferably a detersive material which imparts to the composition detersive and foaming properties. Suitable surfactants are safe and effective amounts of anionic, cationic, nonionic, zwitterionic, amphoteric and betaine surfactants, such as sodium lauryl sulfate, sodium dodecyl benzene sulfonate, alkali metal or ammonium salts of lauroyl sarcosinate, myristoyl sarcosinate, palmitoyl sarcosinate, stearoyl sarcosinate and oleoyl sarcosinate, polyoxyethylene sorbitan monostearate, isostearate and laurate, sodium lauryl sulfoacetate, N-lauroyl sarcosine, the sodium, potassium, and ethanolamine salts of N-lauroyl, N-myristoyl, or N-palmitoyl sarcosine, polyethylene oxide condensates of alkyl phenols, cocoamidopropyl betaine, lauramidopropyl betaine, palmityl betaine and the like. Sodium lauryl sulfate is a preferred surfactant. The oral care composition can comprise from about 0.1% to about 15%, from about 0.3% to about 5%, or from about 0.3% to about 2.5%, by weight of the composition, of the surfactant.

Polyphosphate

The oral care composition can comprise a polyphosphate. The polyphosphate can comprise one or more polyphosphate molecules. Polyphosphates are a class of materials obtained by the dehydration and condensation of orthophosphate to yield linear and cyclic polyphosphates of varying chain lengths. Thus, polyphosphate molecules are generally identified with an average number (n) of polyphosphate molecules, as described below. A polyphosphate is generally understood to consist of two or more phosphate molecules arranged primarily in a linear configuration, although some cyclic derivatives may be present.

Preferred polyphosphates are those having an average of two or more phosphate groups so that surface adsorption at effective concentrations produces sufficient non-bound phosphate functions, which enhance the anionic surface charge as well as hydrophilic character of the surfaces. Preferred in this invention are the linear polyphosphates having the formula: $XO(XPO_3)_nX$, wherein X is sodium, potassium, ammonium, or any other alkali metal cations and n averages from about 2 to about 21. Alkali earth metal cations, such as calcium, are not preferred because they tend to form insoluble fluoride salts from aqueous solutions comprising a fluoride ions and alkali earth metal cations. Thus, the oral care compositions disclosed herein can be free of or substantially free of calcium pyrophosphate.

Some examples of suitable polyphosphate molecules include, for example, pyrophosphate (n=2), tripolyphosphate (n=3), tetrapolyphosphate (n=4), sodaphos polyphosphate (n=6), hexaphos polyphosphate (n=13), benephos polyphosphate (n=14), hexametaphosphate (n=21), which is also known as Glass H. Polyphosphates can include those polyphosphate compounds manufactured by FMC Corporation, ICL Performance Products, and/or Astaris.

The oral care composition can comprise from about 0.01% to about 15%, from about 0.1% to about 10%, from about 0.5% to about 5%, from about 1 to about 20%, or about 10% or less, by weight of the oral care composition, of the polyphosphate.

Other Ingredients

The oral care composition can comprise a variety of other ingredients. Flavoring agents also can be added to the oral care compositions. Suitable flavoring agents include, but are not limited to, oil of wintergreen, oil of peppermint, oil of spearmint, oil of *sassafras*, and oil of clove, cinnamon, anethole, menthol, thymol, eugenol, eucalyptol, lemon, orange and other such flavor compounds to add fruit notes, spice notes, etc. These flavoring agents generally comprise mixtures of aldehydes, ketones, esters, phenols, acids, and aliphatic, aromatic and other alcohols.

Sweeteners can be added to the oral care composition to impart a pleasing taste to the product. Suitable sweeteners include saccharin (as sodium, potassium or calcium saccharin), cyclamate (as a sodium, potassium or calcium salt), acesulfame-K, thaumatin, neohesperidin dihydrochalcone, ammoniated glycyrrhizin, dextrose, levulose, sucrose, sucralose, mannose, and glucose.

Colorants can be added to improve the aesthetic appearance of the product. Suitable colorants include without limitation those colorants approved by appropriate regulatory bodies such as the FDA and those listed in the European Food and Pharmaceutical Directives and include pigments, such as $TiO_2$, and colors such as FD&C and D&C dyes.

Preservatives also can be added to the oral care compositions to prevent bacterial growth. Suitable preservatives approved for use in oral compositions such as methylparaben, propylparaben and sodium benzoate can be added in safe and effective amounts.

Chelants may also be added to temporarily chelate to stannous ions to prevent the oxidation from stannous ions to stannic ions, which are not as effective at providing antibacterial benefits in the oral cavity. Suitable chelants herein include $C_2$-$C_6$ dicarboxylic and tricarboxylic acids, such as succinic acid, malic acid, tartaric acid and citric acid; $C_3$-$C_6$ monocarboxylic acids substituted with hydroxyl, such as gluconic acid; picolinic acid; amino acids such as glycine; phytic acid, salts thereof and mixtures thereof. Also suitable are tripolyphosphates. Longer chain linear polyphosphates, though good chelants, are susceptible to hydrolysis in aqueous compositions. Upon hydrolysis they form orthophosphates which form insoluble zinc complexes.

Other ingredients can be used in the oral care composition, such as desensitizing agents, healing agents, other caries preventative agents, chelating/sequestering agents, vitamins, amino acids, proteins, other anti-plaque/anti-calculus agents, opacifiers, antibiotics, anti-enzymes, enzymes, pH control agents, oxidizing agents, antioxidants, and the like.

Method of Use of Oral Care Compositions

The present invention also relates to methods for reducing plaque, gingivitis, and tooth sensitivity. The method of treatment comprises contacting a subject's oral cavity or at least one tooth with the oral care compositions described herein. The benefits of these compositions may increase over time when the composition is repeatedly used.

The method of treatment may be by brushing with a dentifrice or rinsing with a dentifrice slurry or mouthrinse. Other methods include contacting the topical oral gel, dentures product, mouthspray, or other form with the subject's teeth and oral mucosa. The subject may be any person or lower animal whose oral cavity or at least one tooth contact the oral composition.

Method for Determining the Antimicrobial Efficacy of a Composition

The present invention also relates to methods for determining the antimicrobial efficacy of a composition. A container or vial can be provided comprising a main chamber and a second chamber associated with the main chamber. The main chamber and the second chamber can be in fluid communication.

The main chamber can comprise a liquid growth media. The second chamber can comprise a semi solid or solid growth media, such as agar. The second chamber can comprise a pH indicator dye. The container can be a Soleris® Total Viable Count (NF-TVC) vial.

The detection time of a treated sample can be determined by placing a source of microorganisms, which had been treated with a composition comprising an antimicrobial agent in the main chamber of the container. The container can be placed in a suitable instrument for detecting changes in the color of the second chamber. The detection time in hours is recorded as the time when microorganisms are detected in the containers via a colorimetric reaction between the acidic products created by microorganisms and the pH indicator dye. The detection time is the time it takes for the pH indicator dye to change the color of the second chamber of the container. The longer the detection time, the fewer number of surviving microorganisms that were placed in the main chamber.

The detection time of an untreated sample can be determined by placing a source of microbes into the main chamber of the container. The container can be placed in a suitable instrument for detecting changes in the color of the second chamber. The detection time in hours is recorded as the time when microorganisms are detected in the containers via a colorimetric reaction between the acidic products created by microorganisms and the pH indicator dye. The detection time is the time it takes for the pH indicator dye to change the color of the second chamber of the container. The longer the detection time, the fewer number of surviving and/or inhibited microorganisms that were placed in the main chamber.

The detection time of the untreated sample can be compared with the treated sample. The longer the detection time of the treated sample, the fewer number of surviving mircoorganisms, and the higher the efficacy of the antimicrobial agent in the composition.

The source of microorganisms can be a body fluid, such as, for example, saliva, sweat, or blood, a biological sample, such as, for example, mucous, hair, skin tissue, or organ tissue, or any other source of microorganisms.

The antimicrobial agent can be any suitable antimicrobial agent, a metal ion, an antibiotic, a soluble tin ion, or any other suitable compound that can prevent or stop the growth of microorganisms.

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

Experimental Methods

The multipoint BET surface areas disclosed herein were determined on a Micromeritics TriStar II 3020 V1.03, using the BET nitrogen adsorption method of Brunaur et al., J. Am. Chem. Soc., 60, 309 (1938).

Mercury total intruded volumes were measured on a Micromeritics AutoPore IV 9520, previously calibrated with a silica-alumina reference material available from Micromeritics. As generally known (see Halsey, G. D., J. Chem. Phys. (1948), 16, 931), the mercury porosimetry technique is based on the intrusion of mercury into a porous structure under stringently controlled pressures. From the pressure versus intrusion data, the instrument generates volume and size distributions using the Washburn equation. Since mercury does not wet most substances and will not spontaneously penetrate pores by capillary action, it must be forced into the pores by the application of external pressure. The required pressure is inversely proportional to the size of the pores, and only slight pressure is required to intrude mercury into large macropores, whereas much greater pressures are required to force mercury into micropores. Higher pressures are required to measure the pore sizes and surface areas of the micropores present on the surfaces of silica products disclosed herein.

The total intruded volume (HgI) was measured by mercury porosimetry using a Micromeritics Autopore IV 9520. Samples were dried at 105° C. for two hours prior to analysis. The pore diameters were calculated by the Washburn equation employing a contact angle Theta ($\theta$) equal to 130° and a surface tension gamma equal to 484 dynes/cm. Mercury was forced into the voids of the material (both internal and intraparticle porosity) as a function of pressure, and the volume of the mercury intruded per gram of sample was calculated at each pressure setting. Total mercury intrusion pore volume expressed herein represents the cumulative volume of mercury intruded at pressures from vacuum to 60,000 psi. Increments in volume ($cm^3/g$) at each pressure setting were plotted against the pore radius or diameter corresponding to the pressure setting increments. The peak in the intruded volume versus pore radius or diameter curve corresponds to the mode in the pore size distribution and identifies the most common pore size in the sample. Specifically, sample size was adjusted to achieve a stem volume of 30-50% in a powder penetrometer with a 5 mL bulb and a stem volume of about 1.1 mL. Samples were evacuated to a pressure of 50 µm of Hg and held for 5 minutes. Mercury filled the pores from 4 to 60,000 psi with a 10 second equilibrium time at each of approximately 150 data collection points.

CTAB surface areas disclosed herein were determined by absorption of CTAB (cetyltrimethylammonium bromide) on the silica surface, the excess separated by centrifugation and the quantity determined by titration with sodium lauryl sulfate using a surfactant electrode. Specifically, about 0.5 grams of the silica particles were placed in a 250-mL beaker with 100 mL CTAB solution (5.5 g/L), mixed on an electric stir plate for 1 hour, then centrifuged for 30 min at 10,000 RPM. One mL of 10% Triton X-100 was added to 5 mL of the clear supernatant in a 100-mL beaker. The pH was adjusted to 3-3.5 with 0.1 N HCl and the specimen was titrated with 0.01 M sodium lauryl sulfate using a surfactant electrode (Brinkmann SUR1501-DL) to determine the endpoint.

The median particle size (d50) refers to the particle size for which 50% of the sample has a smaller size and 50% of the sample has a larger size. Median particle size (d50), mean particle size (average), d90, and d10 were determined via the laser diffraction method using a Horiba LA 300 instrument. Samples were de-agglomerated using ultrasonic vibration for 2 minutes.

For pour density and pack density, 20 grams of the sample were placed into a 250 mL graduated cylinder with a flat rubber bottom. The initial volume was recorded and used to calculate the pour density by dividing it into the weight of sample used. The cylinder was then placed onto a tap density machine where it was rotated on a cam at 60 RPM. The cam is designed to raise and drop the cylinder a distance of 5.715 cm once per second, until the sample volume is constant, typically for 15 min. This final volume was recorded and used to calculate the pack density by dividing it into the weight of sample used.

The Einlehner abrasion value is a measure of the hardness/abrasiveness of silica particles, and is described in detail in U.S. Pat. No. 6,616,916, incorporated herein by reference, and involves an Einlehner AT-1000 Abrader generally used as follows: (1) a Fourdrinier brass wire screen is weighed and exposed to the action of a 10% aqueous silica suspension for a fixed length of time; (2) the amount of abrasion is then determined as milligrams of brass lost from the Fourdrinier wire screen per 100,000 revolutions (mg lost/100,000 revolutions).

Salivary Bacteria Inhibition

The in vitro Soleris® assay is a technique for rapidly analyzing the antimicrobial efficacy of oral care actives. In this method, human saliva is exposed to treatments for a set amount of time to mimic normal use. Following treatment, surviving salivary microbes can grow within Soleris® Total Viable Count (NF-TVC) vials until detected by the Soleris® 128 instrument. Comparison of this detection time to detection times of untreated saliva allows for an approximation of microbial reduction (or antimicrobial efficacy) for each treatment. Since soluble tin ions are antimicrobial agents, the antimicrobial efficacy of each composition is a representation of the available soluble tin ions.

Salivary bacteria inhibition was determined by a Soleris® instrument (Neogen Corp., Lansing, Mich., Soleris® 128). A saliva curve was created by first collecting saliva on day 1 from a panel of at least 5 people by paraffin stimulation. The stored saliva was refrigerated at 4° C. until needed. The collected saliva was pooled and mixed thoroughly prior to storage. Immediately prior to use, the saliva was diluted 1:1 with saline and stored on ice.

Next, the 50% diluted saliva was used to prepare a serial dilution of saliva. 900 µL of sterile saline (Baxter 0.9% Sodium Chloride Irrigation, USP, or equivalent Saline solution) was pipetted into 4 separate 1.5 ml microcentrifuge tubes labeled 1 (0.1×), 2 (0.01×), 3 (0.001×) and 4 (0.0001×). 100 µL of 50% diluted saliva was added to tube 1 and vortex mixed for 5 seconds. 100 µL of the contents of tube 1 was placed into tube 2 and vortex mixed for 5 seconds. 100 µL of the contents of tube 2 was placed into tube 3 and vortex mixed for 5 seconds. Finally, 100 µL of the contents of tube 3 was placed into tube 4 and vortex mixed for 5 seconds. 100 µL from each of tubes 1-4 were placed in corresponding Total Viable Count (Neogen Corp., Lansing, Mich., # NF-TVC) vials. NF-TVC vials are pre-filled, ready-to-use vials that in conjunction with the Soleris® equipment and software measure microbial growth by monitoring pH changes and other biochemical reactions. The NF-TVC vials were inverted and were placed in the Soleris® 128 and the program was run to create a standard curve. The program used was NF-TVC 35 with a shuteye of 10, temperature of 35° C., specification of <cfu/gram, a threshold of 50, and a run time of 24 hours.

For testing a mouth rinse formulation, the mouthrinse is added neat. For testing a dentifrice formulation, the dentifrice is diluted by adding 15 g of sterile water to 5 g of dentifrice. The dentifrice slurry was mixed using a homogenizer (BioS pec Products, Bartlesville, Okla., #1281) on high speed for several seconds in a beaker. The homogenizer was rinsed between sample mixing to remove all residue from previously mixed treatment product to prevent carryover.

To prepare samples for analysis, 900 µL of 50% diluted saliva was pipetted into an autoclaved 1.5 mL microcentrifuge tube. The 50% diluted saliva was vortex mixed. Next, a 100 µL sample of either a neat mouth rinse or dentifrice slurry, as prepared above, was added to the microcentrifuge tube. A 2 minute timer was started. The microcentrifuge tube was vortex mixed for 5 seconds. Once the 2 minute timer has completed, 100 µL of the contents of the microcentrifuge tube was pipetted into a Soleris® NF-TVC vial. The contents were inverted and placed in the Soleris® 128. Each sample was replicated three times with three different saliva pools.

Crest® Gum Care was utilized as a positive control. Crest® Cavity Protection was utilized as a negative control. Crest® Pro Health Advanced was utilized as an internal control (or moderately performing). The Soleris® 128 collects optical data for each vial at a rate of 10 readings per hour (i.e. every 6 minutes) to determine whether microorganisms are detected or not. The detection time in hours is recorded as the time when microorganisms are detected in the vials via a colorimetric reaction. The longer the detection time, the fewer number of surviving microorganisms.

TABLE 1

Dentifrice Formulations 1-A through 1-G

| (wt %) | 1-A | 1-B | 1-C | 1-D | 1-E | 1-F | 1-G |
|---|---|---|---|---|---|---|---|
| Glycerin | 56.446 | 56.446 | 61.446 | 61.446 | 61.586 | 61.656 | 61.726 |
| Carrageenan | 0.300 | 0.300 | 0.300 | 0.300 | 0.300 | 0.300 | 0.300 |
| Xanthan Gum | 0.250 | 0.250 | 0.250 | 0.250 | 0.250 | 0.250 | 0.250 |
| SLS (28%)[a] | 3.400 | 3.400 | 3.400 | 3.400 | 3.400 | 3.400 | 3.400 |
| Cocamidopropyl Betaine (30%)[b] | 0.500 | 0.500 | 0.500 | 0.500 | 0.500 | 0.500 | 0.500 |
| Flavor | 1.100 | 1.100 | 1.100 | 1.100 | 1.100 | 1.100 | 1.100 |
| Low Surface Area Silica | 0 | 10.000 | 0 | 15.000 | 15.000 | 15.000 | 15.000 |
| Silica Z119 | 10.000 | 10.000 | 0 | 0 | 0 | 0 | 0 |
| Silica Z109 | 10.000 | 0 | 15.000 | 0 | 0 | 0 | 0 |
| $SnF_2$ | 0.454 | 0.454 | 0.454 | 0.454 | 0.454 | 0.454 | 0.454 |
| $SnCl_2 \cdot 2H_2O$ | 0.280 | 0.280 | 0.280 | 0.280 | 0.140 | 0.070 | 0 |
| Saccharin Na USP | 0.500 | 0.500 | 0.500 | 0.500 | 0.500 | 0.500 | 0.500 |
| Sodium gluconate | 1.170 | 1.170 | 1.170 | 1.170 | 1.170 | 1.170 | 1.170 |
| $TiO_2$ | 0.500 | 0.500 | 0.500 | 0.500 | 0.500 | 0.500 | 0.500 |
| Sodium Hexametaphosphate | 14.000 | 14.000 | 14.000 | 14.000 | 14.000 | 14.000 | 14.000 |
| $Na_3PO_4 \cdot 12H_2O$ | 1.100 | 1.100 | 1.100 | 1.100 | 1.100 | 1.100 | 1.100 |
| Total | 100 | 100 | 100 | 100 | 100 | 100 | 100 |

[a]28 wt % Solution of Sodium Lauryl Sulfate in water

[b]30 wt % of cocamidopropyl betaine in water

TABLE 2

Dentifrice Formulations 2-A through 2-G

| (wt %) | 2-A | 2-B | 2-C | 2-D | 2-E | 2-F | 2-G |
|---|---|---|---|---|---|---|---|
| Glycerin | 35.535 | 35.535 | 46.234 | 46.234 | 46.491 | 46.619 | 46.747 |
| Carrageenan | 0.600 | 0.600 | 0.600 | 0.600 | 0.600 | 0.600 | 0.600 |
| Xanthan Gum | 0.250 | 0.250 | 0.250 | 0.250 | 0.250 | 0.250 | 0.250 |
| SLS (28%)[a] | 3.400 | 3.400 | 3.400 | 3.400 | 3.400 | 3.400 | 3.400 |
| Propylene Glycol | 7.000 | 7.000 | 7.000 | 7.000 | 7.000 | 7.000 | 7.000 |
| PEG 300 | 7.000 | 7.000 | 7.000 | 7.000 | 7.000 | 7.000 | 7.000 |
| Flavor | 1.200 | 1.200 | 1.200 | 1.200 | 1.200 | 1.200 | 1.200 |
| Low Surface Area Silica | 0 | 17.500 | 0 | 15.000 | 15.000 | 15.000 | 15.000 |
| Silica Z119 | 7.449 | 7.449 | 0 | 0 | 0 | 0 | 0 |
| Silica Z109 | 17.500 | 0 | 15.000 | 0 | 0 | 0 | 0 |
| Thickening Silica Z165 | 0.750 | 0.750 | 0 | 0 | 0 | 0 | 0 |
| $SnF_2$ | 0.454 | 0.454 | 0.454 | 0.454 | 0.454 | 0.454 | 0.454 |
| $SnCl_2 \cdot 2H_2O$ | 0.513 | 0.513 | 0.513 | 0.513 | 0.257 | 0.128 | 0 |
| FD&C Blue 1 | 0.050 | 0.050 | 0.050 | 0.050 | 0.050 | 0.050 | 0.050 |
| $TiO_2$ | 0.500 | 0.500 | 0.500 | 0.500 | 0.500 | 0.500 | 0.500 |
| Saccharin Na | 0.700 | 0.700 | 0.700 | 0.700 | 0.700 | 0.700 | 0.700 |
| Sodium gluconate | 1.099 | 1.099 | 1.099 | 1.099 | 1.099 | 1.099 | 1.099 |
| Zn Lactate Dihydrate | 1.900 | 1.900 | 1.900 | 1.900 | 1.900 | 1.900 | 1.900 |
| Sodium Hexametaphosphate | 13.000 | 13.000 | 13.000 | 13.000 | 13.000 | 13.000 | 13.000 |
| $Na_3PO_4 \cdot 12H_2O$ | 1.100 | 1.100 | 1.100 | 1.100 | 1.100 | 1.100 | 1.100 |
| Total | 100 | 100 | 100 | 100 | 100 | 100 | 100 |

[a]28 wt % Solution of Sodium Lauryl Sulfate in water

TABLE 3A

Dentifrice Formulations 3-A through 3-H

| (wt %) | 3-A | 3-B | 3-C | 3-D | 3-E | 3-F | 3-G | 3-H |
|---|---|---|---|---|---|---|---|---|
| Sorbitol | 48.000 | 48.000 | 48.590 | 48.590 | 45.590 | 45.590 | 45.871 | 46.011 |
| Water | 21.131 | 20.081 | 20.081 | 20.081 | 20.081 | 20.081 | 20.081 | 20.081 |
| $SnF_2$ | 0.454 | 0.454 | 0.454 | 0.454 | 0.454 | 0.454 | 0.454 | 0.454 |
| $SnCl_2$[a] | 0.562 | 0.562 | 0.562 | 0.562 | 0.562 | 0.562 | 0.281 | 0.141 |
| Sodium Gluconate | 1.300 | 1.300 | 1.300 | 1.300 | 1.300 | 1.300 | 1.300 | 1.300 |
| NaOH[b] | 0.870 | 0.870 | 0.870 | 0.870 | 0.870 | 0.870 | 0.870 | 0.870 |
| Saccharin | 0.400 | 0.400 | 0.400 | 0.400 | 0.400 | 0.400 | 0.400 | 0.400 |
| Sucralose | 0.200 | 0.200 | 0.200 | 0.200 | 0.200 | 0.200 | 0.200 | 0.200 |
| Xanthan Gum | 0.875 | 0.875 | 0.660 | 0.660 | 0.660 | 0.660 | 0.660 | 0.660 |
| Carrageenan | 1.500 | 1.500 | 1.125 | 1.125 | 1.125 | 1.125 | 1.125 | 1.125 |
| Zinc Citrate | 0.533 | 0.533 | 0.533 | 0.533 | 0.533 | 0.533 | 0.533 | 0.533 |
| Sodium Citrate | 0 | 1.050 | 1.050 | 1.050 | 1.050 | 1.050 | 1.050 | 1.050 |
| $TiO_2$ | 0.500 | 0.500 | 0.500 | 0.500 | 0.500 | 0.500 | 0.500 | 0.500 |
| Flavor | 1.175 | 1.175 | 1.175 | 1.175 | 1.175 | 1.175 | 1.175 | 1.175 |
| SLS | 5.000 | 5.000 | 5.000 | 5.000 | 5.000 | 5.000 | 5.000 | 5.000 |
| Silica Z109 | 17.500 | 17.500 | 17.500 | 0 | 17.500 | 0 | 0 | 0 |
| Thickening Silica Z165 | 0 | 0 | 0 | 0 | 3.000 | 3.000 | 3.000 | 3.000 |
| Low Surface Area Silica | 0 | 0 | 0 | 17.500 | 0 | 17.500 | 17.500 | 17.500 |
| Total | 100 | 100 | 100 | 100 | 100 | 100 | 100 | 100 |

[a]Stannous Chloride with 10% silica blend
[b]50 wt % solution in water

TABLE 3B

Dentifrice Compositions 3-I to 3-P

| (wt %) | 3-I | 3-J | 3-K | 3-L | 3-M | 3-N | 3-O | 3-P |
|---|---|---|---|---|---|---|---|---|
| Sorbitol | 46.152 | 46.188 | 46.468 | 43.590 | 44.188 | 44.468 | 50.139 | 49.685 |
| Water | 20.081 | 20.081 | 20.081 | 20.081 | 20.081 | 20.081 | 20.081 | 20.081 |
| $SnF_2$ | 0.454 | 0.454 | 0.454 | 0.454 | 0.454 | 0.454 | 0.454 | 0.454 |
| $SnCl_2$[a] | 0 | 0.562 | 0.281 | 0.562 | 0.562 | 0.281 | 0 | 0 |
| Sodium Gluconate | 1.300 | 1.300 | 1.300 | 1.300 | 1.300 | 1.300 | 1.300 | 1.300 |
| NaOH (50%)[b] | 0.870 | 0.870 | 0.870 | 0.870 | 0.870 | 0.870 | 0.870 | 0.870 |
| Saccharin | 0.400 | 0.400 | 0.400 | 0.400 | 0.400 | 0.400 | 0.400 | 0.400 |
| Sucralose | 0.200 | 0.200 | 0.200 | 0.200 | 0.200 | 0.200 | 0.200 | 0.200 |

TABLE 3B-continued

| | Dentifrice Compositions 3-I to 3-P | | | | | | | |
|---|---|---|---|---|---|---|---|---|
| (wt %) | 3-I | 3-J | 3-K | 3-L | 3-M | 3-N | 3-O | 3-P |
| Xanthan Gum | 0.660 | 0.438 | 0.438 | 0.660 | 0.438 | 0.438 | 0.660 | 0.660 |
| Carrageenan | 1.125 | 0.750 | 0.750 | 1.125 | 0.750 | 0.750 | 1.125 | 1.125 |
| Zinc Citrate | 0.533 | 0.533 | 0.533 | 0.533 | 0.533 | 0.533 | 0 | 0 |
| Sodium Citrate | 1.050 | 1.050 | 1.050 | 1.050 | 1.050 | 1.050 | 1.050 | 1.050 |
| $TiO_2$ | 0.500 | 0.500 | 0.500 | 0.500 | 0.500 | 0.500 | 0.500 | 0.500 |
| Flavor | 1.175 | 1.175 | 1.175 | 1.175 | 1.175 | 1.175 | 1.175 | 1.175 |
| SLS | 5.000 | 5.000 | 5.000 | 5.00 | 5.00 | 5.00 | 5.00 | 5.00 |
| Silica Z109 | 0 | 0 | 0 | 0 | 0 | 0 | 0 | 0 |
| Thickening Silica Silica Z165 | 3.000 | 3.000 | 3.000 | 5.000 | 5.000 | 5.000 | 0 | 0 |
| Low Surface Area Silica | 17.500 | 17.500 | 17.500 | 17.500 | 17.500 | 17.500 | 17.500 | 17.500 |
| Total | 100 | 100 | 100 | 100 | 100 | 100 | 100 | 100 |

[a]Stannous Chloride with 10% silica blend
[b]50 wt % solution in water

TABLE 4

| | Salivary Inhibition and Selected Components 1-A through 1-G | | | | | | |
|---|---|---|---|---|---|---|---|
| (wt %) | 1-A | 1-B | 1-C | 1-D | 1-E | 1-F | 1-G |
| Low Surface Area Silica | 0 | 10 | 0 | 15 | 15 | 15 | 15 |
| Silica Z119 | 10 | 10 | 0 | 0 | 0 | 0 | 0 |
| Silica Z109 | 10 | 0 | 15 | 0 | 0 | 0 | 0 |
| SnF2 | 0.454 | 0.454 | 0.454 | 0.454 | 0.454 | 0.454 | 0.454 |
| $SnCl_2 \cdot 2H_2O$ | 0.280 | 0.280 | 0.280 | 0.280 | 0.140 | 0.070 | 0 |
| Detection Time (hr) | 5.28 | 5.52 | 5.80 | 6.37 | 6.08 | 6.13 | 5.68 |

TABLE 5

| | Salivary Inhibition and Selected Components of 2-A through 2-G | | | | | | |
|---|---|---|---|---|---|---|---|
| (wt %) | 2-A | 2-B | 2-C | 2-D | 2-E | 2-F | 2-G |
| Low Surface Area Silica | 0 | 17.5 | 0 | 15 | 15 | 15 | 15 |
| Silica Z119 | 7.449 | 7.449 | 0 | 0 | 0 | 0 | 0 |
| Silica Z109 | 17.50 | 0 | 15 | 0 | 0 | 0 | 0 |
| Thickening Silica | 0.75 | 0.75 | 0 | 0 | 0 | 0 | 0 |
| $SnF_2$ | 0.454 | 0.454 | 0.454 | 0.454 | 0.454 | 0.454 | 0.454 |
| $SnCl_2 \cdot 2H_2O$ | 0.513 | 0.513 | 0.513 | 0.513 | 0.257 | 0.128 | 0 |
| Detection Time (hr) | 6.42 | 6.18 | 6.45 | 7.38 | 6.90 | 6.57 | 6.47 |

Formulations for dentifrice compositions 1-A through 1-G are listed in TABLE 1. Dentifrice compositions 1-A through 1-G are an anhydrous or low water dentifrice chassis comprising stannous fluoride with varying levels of stannous chloride as the additional tin compound.

Formulations for dentifrice compositions 2-A through 2-G are listed in TABLE 2. Dentifrice compositions 2-A to 2-G are an anhydrous or low water dentifrice chassis comprising stannous fluoride with varying levels of stannous chloride as the additional tin compound.

Formulations for dentifrice compositions 3-A through 3-P are listed in TABLE 3A and TABLE 3B. Dentifrice compositions 3-A to 3-P are a high-water dentifrice chassis comprising stannous fluoride with varying levels of stannous chloride as the additional tin compound.

Figure 2:
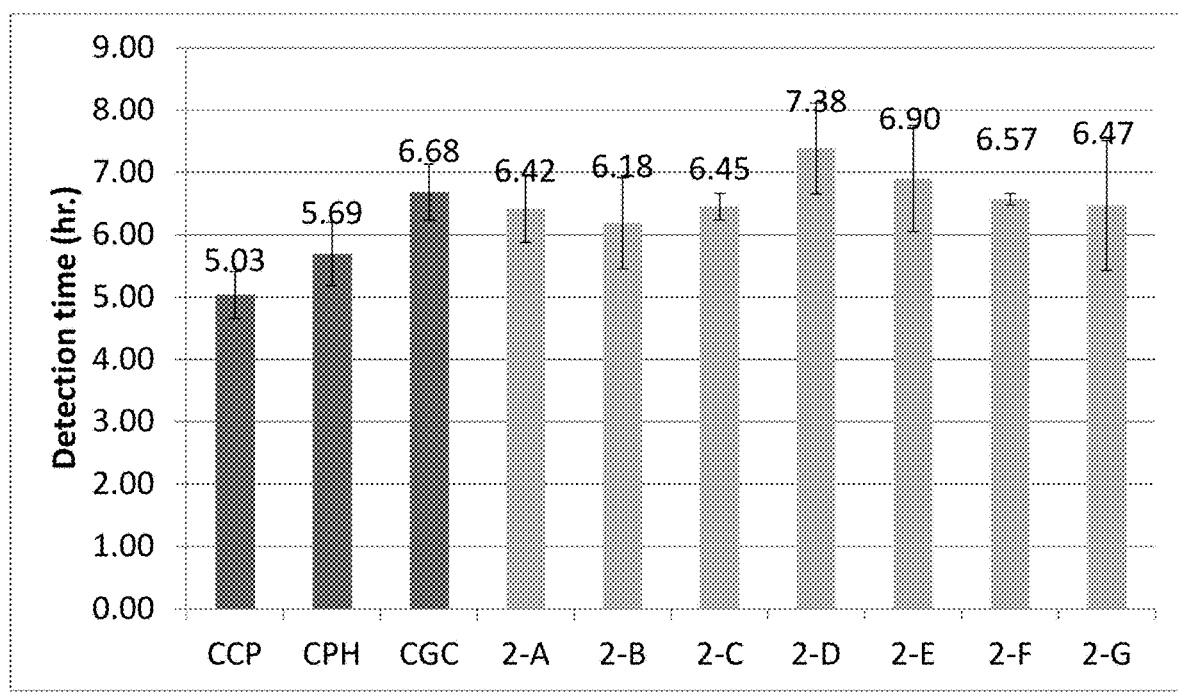
FIG. 2 is a graph showing the salivary bacteria inhibition of 2-A through 2-G.

Salivary bacteria inhibition results are provided in TABLE 4, TABLE 5, FIG. 1 and FIG. 2. TABLE 4 shows that microorganisms will be first apparent in composition 1-A, with 0.28 wt % of stannous chloride and a mixture of Z119 and Z109 silica particles, at 5.28 hr. As shown in compositions 1-B and 1-C, the salivary bacteria inhibition slightly increases when the amount of silica is decreased by 5 wt %. However, when 15 wt % of either Z119 and/or Z109 is replaced with the low surface area silica particles, the salivary bacteria increased to 6.37 hr (composition 1-D) indicating a longer time until the salivary bacteria was measured. Thus, the amount of stannous chloride was reduced to 0.14 wt % (composition 1-E), 0.07 wt % (composition 1-F), and 0 wt % (composition 1-G). Surprisingly, the salivary bacteria inhibition was still 5.6 hr when no amount of stannous chloride was added in composition 1-G, which was longer than the inhibition in 1-A and 1-B, and comparable to the inhibition in 1-C. Thus, the amount of the additional tin compound could be decreased because the surface of the low surface area silica is more compatible and less reactive with tin ions. The longer bacterial inhibition was indicative of a higher bioavailability of soluble tin ions. FIG. 1 shows the detection time of compositions 1-A through 1-G compared with the positive (Crest® Gum Care, GCC, with $SnF_2$ and $SnCl_2$), negative (Crest® Cavity Protection, CCP, without $SnF_2$ and $SnCl_2$), and internal (Crest® Pro-Health™ Advanced, CPH, with $SnF_2$ and $SnCl_2$, but performing between GCC and CCP) controls.

TABLE 5 shows that microorganisms will be first apparent in composition 2-A, with 0.513 wt % of stannous chloride hydrate and a mixture of Z119 and Z109 silica particles, at 6.42 hr. As shown in compositions 2-B and 2-C, the salivary bacteria inhibition slightly increases when the overall amount of silica is decreased. However, when Z119 and/or Z109 is replaced with the low surface area silica particles, the salivary bacteria increased to 7.38 hr (composition 2-D) indicating a longer time until the salivary bacteria was measured. Thus, the amount of stannous chloride was reduced to 0.257 wt % (composition 2-E), 0.128 wt % (composition 2-F), and 0 wt % (composition 2-G). Surprisingly, the salivary bacteria inhibition was still 6.47 hr when no amount of stannous chloride was added in composition 2-G, which was longer than the inhibition in 2-A, 2-B, and 2-C. Thus, the amount of the additional tin compound could be decreased because the surface of the low surface area silica is more compatible and less reactive with soluble tin ions. The longer bacterial inhibition was indicative of a higher bioavailability of tin ions. FIG. 2 shows the detection time of compositions 2-A through 2-G compared with the positive (Crest® Gum Care, GCC, with $SnF_2$ and $SnCl_2$), negative (Crest® Cavity Protection, CCP, without $SnF_2$ and $SnCl_2$), and internal (Crest® Pro-Health™ Advanced, CPH, with $SnF_2$ and $SnCl_2$, but performing between GCC and CCP) controls.

Additionally, composition 2-B had 0.75 wt % of thickening silica (Z165), but still maintained a longer detection time (6.18 hr) compared with the internal and negative controls, as seen in FIG. 2, which indicated that thickening silica could be incorporated into these dentifrice chassis when the low surface area silica particles are utilized in place of other silica particles. The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition comprising:
   (a) from about 0.3% to about 0.6%, by weight of the oral care composition of stannous fluoride;
   (b) less than about 0.2%, by weight of the composition, of an additional tin compound; and
   (c) from about 10% to about 50%, by weight of the composition, of an abrasive comprising spherical silica particles with a sphericity factor (S80) of greater than or equal to about 0.9,
   wherein the spherical silica particles comprise:
      (i) a d50 median particle size in a range from about 8 to about 20 μm;
      (ii) a BET surface area in a range from 0 to about 10 $m^2/g$; and
      (iii) a total mercury intrusion pore volume in a range from about 0.2 to about 1.5 cc/g, and wherein the oral care composition has a detection time of bacteria of greater than or equal to about 5.5 hours.

2. The oral care composition of claim 1, wherein the oral care composition comprises from about 10% to 25%, by weight of the composition, of the abrasive.

3. The oral care composition of claim 1, wherein the additional tin compound comprises stannous chloride.

4. The oral care composition of claim 1, wherein the oral care composition comprises less than about 0.1%, by weight of the composition, of the additional tin compound.

5. The oral care composition of claim 1, wherein the oral care composition is free of the additional tin compound.

6. The oral care composition of claim 1, wherein the composition comprises from about 0.1% to about 30% of polyphosphate.

7. The oral care composition of claim 1, wherein the composition comprises from about 0.1% to about 5% of a citrate source.

8. The oral care composition of claim 1, wherein the composition comprises from about 0.1% to about 15%, by weight of the composition, of thickening silica.

9. An oral care composition comprising:
   (a) from about 0.01% to about 0.5%, by weight of the composition, of stannous chloride;
   (b) a fluoride ion source selected from the group consisting of sodium fluoride, potassium fluoride, amine fluoride, sodium monofluorophosphate, zinc fluoride, and mixtures thereof, (c) from about 10% to about 50%, by weight of the composition, of an abrasive comprising spherical silica particles with a sphericity factor (S80) of greater than or equal to about 0.9,
   wherein the spherical silica particles comprise:
      (i) a d50 median particle size in a range from about 8 to about 20 μm;
      (ii) a BET surface area in a range from 0 to about 10 $m^2/g$; and
      (iii) a total mercury intrusion pore volume in a range from about 0.2 to about 1.5 cc/g, and wherein the oral care composition has a detection time of bacteria of greater than or equal to about 5.5 hours.

10. The oral care composition of claim 9, wherein the oral care composition comprises from about 10% to 25%, by weight of the composition, of the abrasive.

11. The oral care composition of claim 1, wherein the composition comprises from about 0.1% to about 30% of polyphosphate.

12. The oral care composition of claim 1, wherein the composition comprises from about 0.1% to about 5% of a citrate source.

13. A method for reducing plaque, gingivitis, or tooth sensitivity of a subject comprising:
   (a) providing the oral care composition of claim 1; and
   (b) contacting the subject's oral cavity with the oral care composition.

14. The method of claim 13, wherein the oral care composition is free of the additional tin compound.

* * * * *